United States Patent [19]

Ohkawa

[11] Patent Number: 5,169,970

[45] Date of Patent: Dec. 8, 1992

[54] METHOD FOR HYDROLYZING ORGANOCHLOROSILANES

[75] Inventor: Nobuaki Ohkawa, Gunma, Japan

[73] Assignee: Toshiba Silicone Co., Ltd., Tokyo, Japan

[21] Appl. No.: 370,974

[22] Filed: Jun. 26, 1989

[30] Foreign Application Priority Data

Jun. 27, 1988 [JP] Japan ................. 63-160241

[51] Int. Cl.$^5$ ............................... C07F 7/08
[52] U.S. Cl. .................... 556/459; 556/460; 556/461
[58] Field of Search ............ 556/459, 460, 461

[56] References Cited

U.S. PATENT DOCUMENTS

| | | | |
|---|---|---|---|
| 3,489,782 | 1/1970 | Pruvost et al. | 556/459 X |
| 3,595,896 | 7/1971 | Nitzsche et al. | 556/460 X |
| 4,609,751 | 9/1986 | Hajjar | 556/460 X |
| 4,772,737 | 9/1988 | Sartique et al. | 556/459 X |

Primary Examiner—Paul F. Shaver
Attorney, Agent, or Firm—Sughrue, Mion, Zinn, Macpeak & Seas

[57] ABSTRACT

A method for hydrolyzing an organochlorosilane to produce an organopolysiloxane, which comprises
a first-stage hydrolysis of hydrolyzing the organochlorosilane using a substantially stoichiometrically equivalent amount of water, thereby producing a hydrolyzate, and
a second-stage hydrolysis of hydrolyzing the hydrolyzate obtained in the first-state hydrolysis using a stoichiometrically excess amount of aqueous hydrogen chloride solution having a predetermined hydrogen chloride concentration, thereby to produce an organopolysiloxane as a hydrolyzate and, at the same time, regulate the viscosity of the organopolysiloxane.

2 Claims, 1 Drawing Sheet

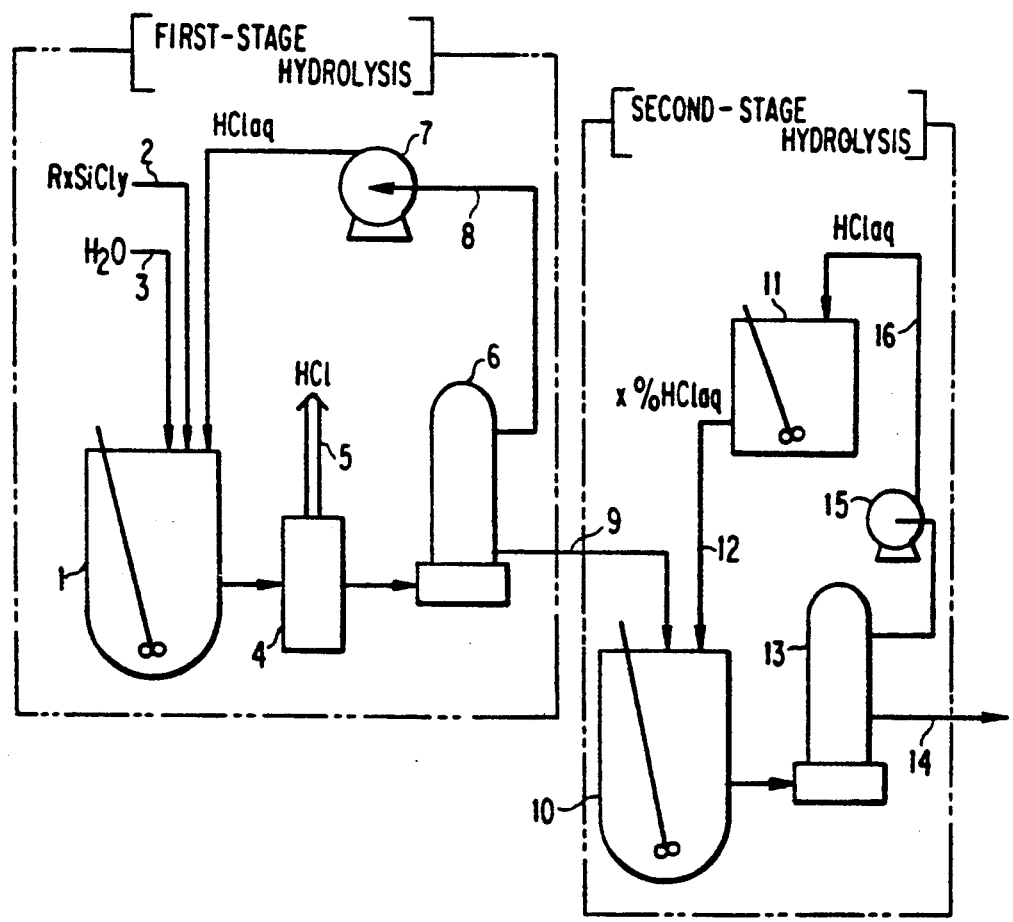

METHOD FOR HYDROLYZING ORGANOCHLOROSILANES

FIELD OF THE INVENTION

This invention relates to a method for hydrolyzing an organochlorosilane. More particularly, the present invention is concerned with a method for hydrolyzing an organochlorosilane, wherein the hydrolysis is conducted in two stages; in the first-stage hydrolysis, an organochlorosilane is hydrolyzed by using an equivalent amount of water and, hence, the hydrolysis and the recovery of the hydrogen chloride generated are conducted at a high thermal efficiency, and then an organopolysiloxane having a desired viscosity is obtained through the second-stage hydrolysis.

BACKGROUND OF THE INVENTION

Hydrolysis of dimethyldichlorosilane has been known as a method for the production of organopolysiloxanes.

For example, a method for hydrolyzing dimethyldichlorosilane in the presence of a stoichiometrically excess amount of water is known as such a hydrolysis method. In general, where hydrolysis is conducted in the presence of an excess of water as in the above method, there are obtained dimethyl cyclopolysiloxane as the main component of the resulting hydrolyzate, and straight-chain, low-molecular-weight dimethyl polysiloxane having silanol groups at both ends as the remainder.

In the above hydrolysis reaction, hydrogen chloride is generated as a by-product, and this hydrogen chloride is recovered in order to react it with methanol to convert it into methyl chloride which is a starting material for the synthesis of dimethyldichlorosilane. Such a method is described in, for example, JP-A-58-69890. (The term "JP-A" as used herein means an "unexamined published Japanese patent application".)

However, since an excess of water is used in the above method, most of the hydrogen chloride generated is necessarily separated in the form of saturated hydrochloric acid. Part of this hydrochloric acid is recycled for use in the hydrolysis, while the remaining part of the aqueous solution of hydrogen chloride is heated to obtain an HCl-H2O azeotropic mixture having a contant boiling point and hydrogen chloride.

That is, the conventional hydrolysis method where dimethyldichlorosilane is hydrolyzed using excess water must require a considerable amount of heat energy for the recovery of hydrogen chloride. Further, where the hydrolysis reaction is conducted in the presence of excess water as in the above method, the reaction system must be cooled because a considerable amount of heat is generated due to the exothermic reaction. Thus, this hydrolysis method is greatly disadvantageous from the standpoint of heat energy.

For the purpose of overcoming the above problems, a method in which dimethyldichlorosilane is hydrolyzed using a stoichiometrically equivalent amount of water has been proposed as described in, for example, JP-A-58-126893.

This hydrolysis method, however, is disadvantageous in that the amount of the hydrogen chloride dissolved in the resulting hydrolyzate becomes large, so that the viscosity of the hydrolyzate becomes high. Furthermore, there is another problem that the hydrolysis reaction cannot proceed sufficiently if conducted in a relatively short period of time, leading to low yields and high production costs.

SUMMARY OF THE INVENTION

As a result of intensive studies to overcome the problems of the prior art methods, it has been found that a desired organopolysiloxane can be obtained most efficiently by a method in which the hydrolysis of an organochlorosilane is conducted in two stages. This invention has been completed based on this finding.

Accordingly, an object of the present invention is to provide a method for hydrolyzing an organochlorosilane to produce an organopolysiloxane, by which method the hydrogen chloride generated as a by-product can be recovered efficiently, the thermal efficiency in the whole hydrolysis process can be heightened, resulting in improved productivity, and further an organopolysiloxane having a desired viscosity can be obtained as a hydrolyzate, thus eliminating the above-described disadvantages of the conventional methods.

The method for hydrolyzing an organochlorosilane to produce an organopolysiloxane according to the present invention comprises a first-stage hydrolysis of hydrolyzing the organochlorosilane using a substantially stoichiometrically equivalent amount of water, thereby producing a hydrolyzate, and a second-stage hydrolysis of hydrolyzing the hydrolyzate obtained in the first-stage hydrolysis using a stoichiometrically excess amount of water coming from an aqueous hydrogen chloride solution have a predetermined hydrogen chloride concentration, thereby to produce an organopolysiloxane as a hydrolyzate and, at the same time, regulate the viscosity of the organopolysiloxane.

BRIEF DESCRIPTION OF THE DRAWING

The FIGURE is a flow chart showing one embodiment of a hydrolysis apparatus to which the method of this invention is applied.

DETAILED DESCRIPTION OF THE INVENTION

The organochlorosilane used in the method of the present invention is a compound represented by the formula

$(R)_a(H)_b SiCl_{4-a-b}$

In the above formula, examples of R include an alkyl group (such as methyl, ethyl, propyl, butyl, pentyl, hexyl, heptyl, octyl, nonyl, decyl, dodecyl), a cycloalkyl group (such as cyclopentyl, cyclohexyl), an aralkyl group (such as 2-phenylethyl, 3-phenylpropyl), an aryl group (such as phenyl, tolyl), an alkenyl group (such as vinyl), and a substituted hydrocarbon group (such as chloromethyl, 3-chloropropyl, chlorophenyl, 3,3,3-trifluoropropyl). Of those, methyl is most preferred from the standpoint that it is particularly stable under strongly acidic conditions.

In the above formula, a is an integer of 1 to 3, b is an integer of 0 to 2, and the sum of a+b is in the range of from 1 to 3. Further, where a is 2 or larger, R may be the same or different.

The method for hydrolyzing an organochlorosilane according to the present invention can be practiced, for example, by means of a hydrolysis apparatus as shown in the FIGURE.

The method of the present invention will be explained below in detail with respect to one embodiment employing the apparatus shown in the FIGURE.

Into a first reactor 1 for first-stage hydrolysis are introduced an organochlorosilane and a stoichiometrically substantially equivalent amount of water, or an aqueous hydrogen chloride solution containing water in such an amount, through raw material-supply pipings 2 and 3, respectively. That is, water is introduced in an amount which is required for the hydrolysis of the organochlorosilane. Specifically, 0.8 to 1.2 molecules, per silicon-bonded chlorine atom in the organochlorosilane, of water is introduced.

Immediately after the introduction of those materials, a reaction begins, with the evolution of anhydrous hydrogen chloride. This anhydrous hydrogen chloride gas is taken out of the reaction system by means of an emission tank 4 through a piping 5, for example, under reduced pressure.

The conditions for this first-stage hydrolysis are not particularly limited. However, it is preferred that the hydrolysis reaction is conducted at a temperature in the range of from −20° C. to 50° C., more preferably from −20° C. to 0° C., by utilizing the fact that the initial reaction is endothermic due to the violent evolution of hydrogen chloride, and also taking into consideration the thermal efficiency, a desired composition of an organopolysiloxane to be obtained, and the yield and purity of anhydrous hydrogen chloride to be generated. Further, the reaction time is varied depending upon the difference in apparatus, etc., between batch production and continuous production, but is generally selected from the range of from 0.5 minute to 60 minutes.

The thus-obtained reaction mixture of an organopolysiloxane which is a hydrolyzate of the first-stage hydrolysis and a saturated aqueous solution of hydrogen chloride is transferred to a separator 6 via the emission tank 4. The saturated aqueous solution of hydrogen chloride separated from the hydrolyzate in this separator 6 is sent to the reactor 1 for first-stage hydrolysis through a piping 8 by means of a circulating pump 7 and reused. On the other hand, the organopolysiloxane hydrolyzate is transferred to a second reactor 10 for second-stage hydrolysis through a supply piping 9.

Into the second reactor 10 for second-stage hydrolysis is introduced, through a raw material-supply piping 12, an aqueous solution of hydrogen chloride whose hydrogen chloride concentration has been regulated at a predetermined value by means of a regulating tank 11 for the aqueous hydrogen chloride solution. The amount of the aqueous hydrogen chloride solution introduced is such that it contains a stoichiometrically equivalent amount or a larger amount of water in order to complete the hydrolysis reaction. In general, the amount of water subjected to the reaction in the second reactor is more than 1.2 equivalent per the stoichiometrically equivalent amount. However, the method of the present invention is advantageous in that the amount of water used in the whole method can be extremely small as compared with the conventional methods.

In this second-stage hydrolysis, the organochlorosilane containing unreacted part, introduced from the first-stage hydrolysis undergoes hydrolysis to generate hydrogen chloride (endothermic reaction), and the hydrogen chloride generates heat when dissolving in a hydrogen chloride aqueous solution. Since the amount of heat generated is larger in the reaction system as a whole, the reaction temperature must be controlled in the range of 10° to 80° C. The reaction temperature affects the viscosity of the organopolysiloxane hydrolyzate and the dissolved hydrogen chloride content, and therefore, is controlled according to the properties of the desired hydrolyzate.

Further, the reaction time varies depending upon the degree of the progress of reaction in the first-stage hydrolysis and the concentration of the hydrogen chloride aqueous solution introduced into the second-stage hydrolysis, but is generally 0.5 to 60 minutes.

After completion of the reaction, the resulting reaction mixture containing an organopolysiloxane as a hydrolyzate is transferred to a separator 13, where the reaction mixture is separated into the organopolysiloxane hydrolyzate and aqueous hydrogen chloride solution. The thus-obtained organopolysiloxane hydrolyzate is transferred to a neutralization tank, not shown in the FIGURE, through a discharge piping 14, while the aqueous hydrogen chloride solution is sent to a regulating tank 11 through a piping 16 by means of a circulating pump 15 and reused.

As described above, the hydrolysis method according to the present invention can be practiced in both continuous production and batch production.

In the first-stage hydrolysis in the method of the present invention, anhydrous hydrogen chloride can be obtained stably and in a high yield by conducting the hydrolysis reaction at a temperature in the range of from −20° to 50° C., preferably, from −20° to 0° C., because the initial reaction is endothermic due to the violent generation of hydrogen chloride. The cyclic polysiloxane and chlorine-terminated linear polysiloxane both obtained in the first-stage hydrolysis are then subjected to the second-stage hydrolysis, where the hydrolysis reactions thereof are completed.

Further, the viscosity of the finally obtained hydrolyzate and the content of hydrogen chloride dissolved therein can be controlled by suitably regulating the hydrogen chloride concentration in the aqueous hydrogen chloride solution to be used in the second-stage hydrolysis at a value in the range of from nearly 0% to a saturated concentration thereof. That is, the composition and proportion of a cyclic compound and the composition and proportion of a hydroxyl-terminated linear organopolysiloxane, both contained in the final hydrolyzate, can be freely controlled within certain ranges by changing the conditions for this second-stage hydrolysis.

As described above, in the method for hydrolyzing an organochlorosilane according to the present invention, the hydrolysis is conducted in two stages. In the first-stage hydrolysis, since a substantially stoichiometrically equivalent amount of water is used for the hydrolysis reaction, the reaction can be conducted at a high thermal efficiency and the hydrogen chloride evolved can be recovered and reused efficiently and stably. Furthermore, the incompletely hydrolyzed product resulting from the first-stage hydrolysis is then subjected to the second-stage hydrolysis which uses an aqueous hydrogen chloride solution whose hydrogen chloride concentration has been suitably regulated at a proper value, whereby the viscosity and composition of an organopolysiloxane to be obtained as the final hydrolyzate can be controlled and, also, the hydrogen chloride concentration in the final hydrolyzate can be made low.

According to the method of the present invention, the hydrogen chloride evolved during the hydrolysis can be recovered efficiently and stably and, further, the viscosity and composition of the organopolysiloxane to be obtained as the final hydrolyzate can be controlled, as described hereinbefore. Therefore, the method of the present invention is extremely effective in obtaining raw materials useful in the silicone industry.

The present invention will now be explained in more detail by reference to the following Examples and Comparative Examples, but the Examples should not be construed to be limiting the scope of the invention. In the Examples and Comparative Examples, all parts are by weight, unless otherwise indicated.

EXAMPLE 1

Using the apparatus as shown in the FIGURE, hydrolysis of dimethyldichlorosilane was conducted as follows.

Into a first reactor 1 for first-stage hydrolysis were continuously introduced 129 parts of dimethyldichlorosilane and 36 parts of water (the molar ratio of the dimethyldichlorosilane to the water being 1:2) through raw material-supply pipings 2 and 3, respectively, over a period of 3 minutes, while the temperature of the reaction system was kept at −5° C. or less. Thereafter, the resulting mixture was stirred for 7 minutes at a temperature of −10° C.

Subsequently, the hydrolysis reaction mixture resulting from this first-stage hydrolysis was fed to an emission tank 4, where the mixture was allowed to sufficiently emit anhydrous hydrogen chloride at about −10° C. under reduced pressure. The anhydrous hydrogen chloride thus emitted was recovered through a piping 5, while the resulting hydrolysis reaction mixture was transferred to a separator 6. As a result of those procedures, the amount of the anhydrous hydrogen chloride recovered was 67.3% of the theoretical amount thereof to be generated from the dimethyldichlorosilane used.

The resulting hydrolysis reaction mixture was separated by means of the separator 6 into dimethyl polysiloxane as a hydrolyzate and a saturated aqueous solution of hydrogen chloride. The dimethyl polysiloxane hydrolyzate thus obtained in the first-stage hydrolysis had a viscosity measured at 25° C. of 2.7 cSt, and titration revealed that this hydrolyzate had a dissolved hydrogen chloride content of 13.1% by weight. This dimethyl polysiloxane hydrolyzate obtained in the first-stage hydrolysis was transferred to a second reactor 10 for second-stage hydrolysis. On the other hand, the saturated aqueous solution of hydrogen chloride, which was to be sent to the first reactor 1 for first-stage hydrolysis by means of a circulating pump 7 and reused, contained hydrogen chloride in an amount of 17.2% of the theoretical amount generated from the dimethyldichlorosilane used.

The temperature of the dimethyl polysiloxane hydrolyzate obtained in the first-stage hydrolysis, which had been transferred to the second reactor 10 for second-stage hydrolysis, was kept at 40° C. Into this second reactor was introduced, over a period of one minute, 100 parts of aqueous hydrogen chloride solution whose hydrogen chloride concentration had been regulated at 5.5% by means of a regulating tank 11 for the aqueous hydrogen chloride solution. The hydrolysis reaction was completed in 5 minutes, throughout which the temperature of the reaction system was kept at 40° C.

Subsequently, the resulting hydrolysis reaction mixture was fed to a separator 13, and separated into dimethyl polysiloxane as a final hydrolyzate and an aqueous hydrogen chloride solution. This dimethyl polysiloxane hydrolyzate was transferred to a neutralization tank, not shown in the FIGURE, through a discharge piping 14, while the aqueous hydrogen chloride solution was to be transferred to the regulating tank 11 for aqueous hydrogen chloride solution through a piping 16 by means of a circulating pump 15 and reused.

The dimethyl polysiloxane thus transferred to the neutralization tank had a viscosity measured at 25° C. of 7.9 cSt and a dissolved hydrogen chloride content of 0.19% by weight, and was found to be composed of 75% of cyclic dimethyl polysiloxane (including 68% cyclic tetramer) and 25% of α,ω-dihydroxypolydimethylsiloxane having terminal hydroxyl groups.

COMPARATIVE EXAMPLE 1

Using part of the apparatus as shown in the FIGURE, only the first-stage hydrolysis was conducted to prepare dimethyl polysiloxane as follows.

Into a reactor 1 for first-stage hydrolysis, 129 parts of dimethyldichlorosilane and 360 parts of water (the molar ratio of the dimethyldichlorosilane to the water being 1:20) were introduced in the same manner as in Example 1. As a result, the temperature in the reaction system was increased rapidly, and finally reached 70° C.

Subsequently, the resulting hydrolysis reaction mixture was separated by means of a separator 6 into dimethyl polysiloxane as a hydrolyzate and a saturated aqueous solution of hydrogen chloride. The thus obtained dimethyl polysiloxane hydrolyzate had a viscosity measured at 25° C. of 5.6 cSt and a dissolved hydrogen chloride content of 0.2%. Further, it was found that this hydrolyzate was composed of 78% of cyclic dimethylpolysiloxane and 22% of α,ω-dihydroxypolydimethylsiloxane. Those analytical results were similar to those obtained in Example 1.

On the other hand, an aqueous solution of hydrogen chloride was recovered, but its hydrogen chloride concentration was as low as 16.9%. Further, in order to recover hydrogen chloride from the hydrogen chloride solution, it was required to employ distillation or other means.

As is apparent from the above results, even only the above first-stage hydrolysis which employed a stoichiometrically excess amount of water could produce dimethyl polysiloxane having substantially the same composition as that in Example 1. However, when taking into consideration the reaction time, temperature control, recovery of hydrogen chloride and others, the above method was far inferior to the method of Example 1 in chemical yield, thermal efficiency, etc.

COMPARATIVE EXAMPLE 2

The dimethyl polysiloxane hydrolyzate which was obtained through only the first-stage hydrolysis in Example 1 and had a viscosity measured at 25° C. of 2.7 cSt and a dissolved hydrogen chloride content of 13.1% by weight was found to have a cyclic dimethyl polysiloxane content of 43.2%, and contain chlorine-terminated α,ω-dichloropolydimethylchlorosilane and dimethyldichlorosilane which remained unreacted, in a total proportion of 10.5% by weight.

Therefore, in the case where the hydrolysis of dimethyldichlorosilane was conducted only through the first-stage hydrolysis using a stoichiometrically equivalent amount of water, the reaction was insufficient and the thus obtained dimethyl polysiloxane was unsuitable for use a material for silicones because it contained a relatively large porportion of chlorine as an impurity.

EXAMPLE 2

A hydrolyzate obtained through first-stage hydrolysis in the same manner as in Example 1 was introduced into a second reactor 10 for second-stage hydrolysis. Into this second reactor was further introduced in the same manner as in Example 1 100 parts of an aqueous hydrogen chloride solution whose hydrogen chloride concentration had been regulated at 18.8% by means of a regulating tank 11 for the aqueous hydrogen chloride solution. The reaction was completed in 10 minutes, and the resulting hydrolysis reaction mixture was transferred to a separator 13, where it was then separated into dimethyl polysiloxane as a hydrolyzate and an aqueous hydrogen chloride solution.

The dimethyl polysiloxane hydrolyzate thus obtained had a viscosity measured at 25° C. of 29.1 cSt and a dissolved hydrogen chloride content of 0.38%, and was found to be composed of 67% of cyclic dimethyl polysiloxane and 33% of $\alpha,\omega$-dihydroxypolydimethylsiloxane.

The temperature was maintained at 10°–80° C. throughout the reaction steps.

EXAMPLE 3

A dimethyl polysiloxane hydrolyzate and an aqueous hydrogen chloride solution were obtained in the same manner as in Example 2 except that the hydrogen chloride concentration of the aqueous hydrogen chloride solution to be introduced into a second reactor 10 for second-stage hydrolysis was regulated at 25%.

The thus obtained dimethyl polysiloxane hydrolyzate had a viscosity measured at 25° C. of 40.6 cSt and a dissolved hydrogen chloride content of 0.85%, and was found to be composed of 49.5% of cyclic dimethyl polysiloxane and 50.5% of $\alpha,\omega$-dihydroxypolydimethylsiloxane.

From the results obtained in Examples 1 to 3, it is apparent that the viscosity and composition of a desired dimethyl polysiloxane to be obtained as a hydrolyzate can be regulated by controlling the conditions for the second-stage hydrolysis.

Further, a comparison between the results of the Examples and those of the Comparative Examples shows that the method of the present invention is superior to the conventional methods in chemical yield, thermal efficiency, etc.

While the invention has been described in detail and with reference to specific embodiments thereof, it will be apparent to one skilled in the art that various changes and modifications can be made therein without departing from the spirit and scope thereof.

What is claimed is:

1. A method for hydrolyzing an organochlorosilane to produce an organopolysiloxane, which comprises
    a first-stage hydrolysis of hydrolyzing the organochlorosilane using a substantially stoichiometrically equivalent amount of water, thereby producing a hydrolyzate, and
    a second-stage hydrolysis of hydrolyzing the hydrolyzate obtained in the first-stage hydrolysis using a stoichiometrically excess amount of an aqueous hydrogen chloride solution having a predetermined hydrogen chloride concentration, thereby to produce an organopolysiloxane as a hydrolyzate and, at the same time, regulate the viscosity of said organopolysiloxane.

2. A method as claimed in claim 1, wherein the hydrolysis reaction in the first-stage hydrolysis is conducted at a temperature in the range of from −20° C. to 0° C.

* * * * *